(12) United States Patent
Pinch (10) Patent No.: US 10,863,973 B2
(45) Date of Patent: Dec. 15, 2020

(54) THERMAL SHUNT FOR TRANSFERRING HEAT FROM A PORTABLE MEDICAL DEVICE TO A STAND

(71) Applicant: FUJIFILM SonoSite, Inc., Bothell, WA (US)

(72) Inventor: Michael Pinch, Seattle, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 0 days.

(21) Appl. No.: 15/688,771

(22) Filed: Aug. 28, 2017

(65) Prior Publication Data

US 2019/0059859 A1  Feb. 28, 2019

(51) Int. Cl.
| | |
|---|---|
| *A61B 8/00* | (2006.01) |
| *A61B 50/13* | (2016.01) |
| *G01S 15/89* | (2006.01) |
| *A61B 50/15* | (2016.01) |

(52) U.S. Cl.
CPC ............ *A61B 8/546* (2013.01); *A61B 8/4405* (2013.01); *A61B 8/4427* (2013.01); *A61B 8/4433* (2013.01); *A61B 8/46* (2013.01); *A61B 50/13* (2016.02); *A61B 50/15* (2016.02); *A61B 2560/0456* (2013.01); *G01S 15/899* (2013.01)

(58) Field of Classification Search
CPC ....... A61B 8/546; A61B 8/4433; A61B 50/13; A61B 8/46; A61B 2560/0456; G06F 19/3418; G06F 1/1632; G06F 19/30; G06F 1/1654; A61G 13/104; A61G 2203/20; G16H 30/20; G16H 50/20; A61M 2209/084; A61M 5/172; A61M 2205/50; A61M 2209/086; H01L 41/053

USPC .......... 361/679.46, 695, 707; 165/80.3, 121, 165/185, 80.2; 454/184
See application file for complete search history.

(56) References Cited

U.S. PATENT DOCUMENTS

| | | | | |
|---|---|---|---|---|
| 5,424,913 | A * | 6/1995 | Swindler .................. | G06F 1/203 361/679.47 |
| 9,778,695 | B1 * | 10/2017 | Shibayama ........... | G06F 1/1632 |
| 2002/0018335 | A1 * | 2/2002 | Koizumi ............... | G06F 1/1632 361/679.47 |

(Continued)

*Primary Examiner* — Mandeep S Buttar
(74) *Attorney, Agent, or Firm* — Womble Bond Dickinson (US) LLP (57) ABSTRACT

A portable medical device, such as an ultrasound imaging system, is configured to connect to a stand, and transfer heat from the device to the stand. The device includes a heat-generating source, a hot plate that is thermally coupled to the heat-generating source, and a barrier plate that is biased away from the hot plate and moveable between a first position, wherein the device is not docked to the stand, and a second position, wherein the device is docked to the stand. In the first position, the barrier plate is not in thermally conductive contact with the hot plate, and in the second position, the barrier plate is in thermally conductive contact with the hot plate. When moved from the first position to the second position, a cold plate on the stand pushes the barrier plate into the second position such that heat generated by the imaging system is transferred through the barrier plate to the hot plate and into a cold plate of the stand. As such, in the second position, the device is configured to transfer heat from the imaging system to the stand via a conductive pathway including at least the hot plate, the barrier plate, and the cold plate.

31 Claims, 7 Drawing Sheets

(56) References Cited

U.S. PATENT DOCUMENTS

| | | | | |
|---|---|---|---|---|
| 2002/0085351 A1* | 7/2002 | Ghosh | .................... | G06F 1/1632 |
| | | | | 361/679.46 |
| 2002/0105783 A1* | 8/2002 | Kitahara | ............... | G06F 1/1632 |
| | | | | 361/695 |
| 2002/0186531 A1* | 12/2002 | Pokharna | .............. | G06F 1/1632 |
| | | | | 361/679.09 |
| 2008/0104300 A1* | 5/2008 | Diener | .................. | G06F 1/1632 |
| | | | | 710/303 |
| 2009/0154079 A1* | 6/2009 | Bae | ........................ | A47B 21/00 |
| | | | | 361/679.02 |
| 2010/0124016 A1* | 5/2010 | Gu | ........................ | G06F 1/1626 |
| | | | | 361/694 |
| 2013/0309899 A1* | 11/2013 | Sehmbey | ................ | G06F 1/203 |
| | | | | 439/485 |
| 2017/0160772 A1* | 6/2017 | Kamimura | ............ | G06F 1/1616 |

* cited by examiner

THERMAL SHUNT FOR TRANSFERRING HEAT FROM A PORTABLE MEDICAL DEVICE TO A STAND

TECHNICAL FIELD

The disclosed technology relates generally to portable medical devices and systems that are mountable to a stand assembly unit. More specifically, the disclosed technology relates to transferring heat from portable medical devices to stand assembly units.

BACKGROUND

Portable medical electrical equipment, such as ultrasound imaging systems, are commonly used while being docked to a stand. The stand provides support for the imaging system, and can allow the device to be charged as it is being used. One drawback, however, of docking an imaging system to a stand is the blocking of the imaging system's cooling systems and/or vents. An imaging system is commonly equipped with one or more fan units used to cool the imaging system as its heat-generating sources heat up during operation. The air from the fan units is blown away from the imaging system through the side or bottom vents to cool the imaging system. When the imaging system is mounted to the stand, the vents of the imaging system can be blocked or constricted and the imaging system is no longer exposed to air flow. This may result in overheating of the imaging system and can decrease the available run time of the imaging system before it needs to cool. As such, the amount of time that an imaging system can spend on the stand is also decreased. This problem is compounded by the fact that stands used to dock imaging systems or other electronic devices are often designed to prevent liquid ingress, and thus do not typically include openings.

One attempted solution to this problem is to add more fans and/or vents to the imaging systems to increase their ability to cool the system even if a portion of the vents are blocked by the stand. This solution, however, is inefficient, and the additional fans create significant noise that can be disturbing to patients, and/or is contrary to industry design standards (e.g., IEC-60601). The additional fans also take up significant physical space in the imaging system, and can require other sacrifices and/or design limitations to be made to accommodate the additional fans. Another drawback of this solution is that cooling merely by fans (i.e., convection) has less thermal capacity to absorb and withdraw heat compared to other cooling means. Accordingly, there is a need to improve the methods and systems currently available for cooling imaging systems when they are mounted to stands. Additionally, the problems associated with cooling imaging systems is expected to become more prevalent as the next generation of systems operate at higher speeds, are equipped with greater processing power, and generate more heat. The newer imaging systems are expected to be significantly larger (e.g., heavier), and thus will likely spend more time docked to a stand than traditional, smaller imaging systems. For at least these reasons, there exists a need to better cool portable medical devices, especially when mounted to a stand.

DETAILED DESCRIPTION

The technology disclosed herein relates to methods and systems for transferring heat to a stand from a portable ultrasound imaging system that is mounted thereon. Although the technology is described with respect to its use with ultrasound imaging systems, it will be appreciated that the technology can also be used in any other suitable electronic device such as, for example, patient monitors, defibrillators, EKG machines, mobile devices, tablets, laptop computers, and/or any other device that sometimes uses a cordless power source and/or is sometimes docked.

For ease of reference, throughout this disclosure identical reference numbers are used to identify similar or analogous components or features, but the use of the same reference number does not imply that the parts should be construed to be identical. Indeed, in many examples described herein, the identically-numbered parts may be distinct in structure and/or function. Furthermore, the same shading may be used to indicate materials in a cross section that can be compositionally similar, but the use of the same shading does not imply that the materials should be construed to be identical.

Figure 1:
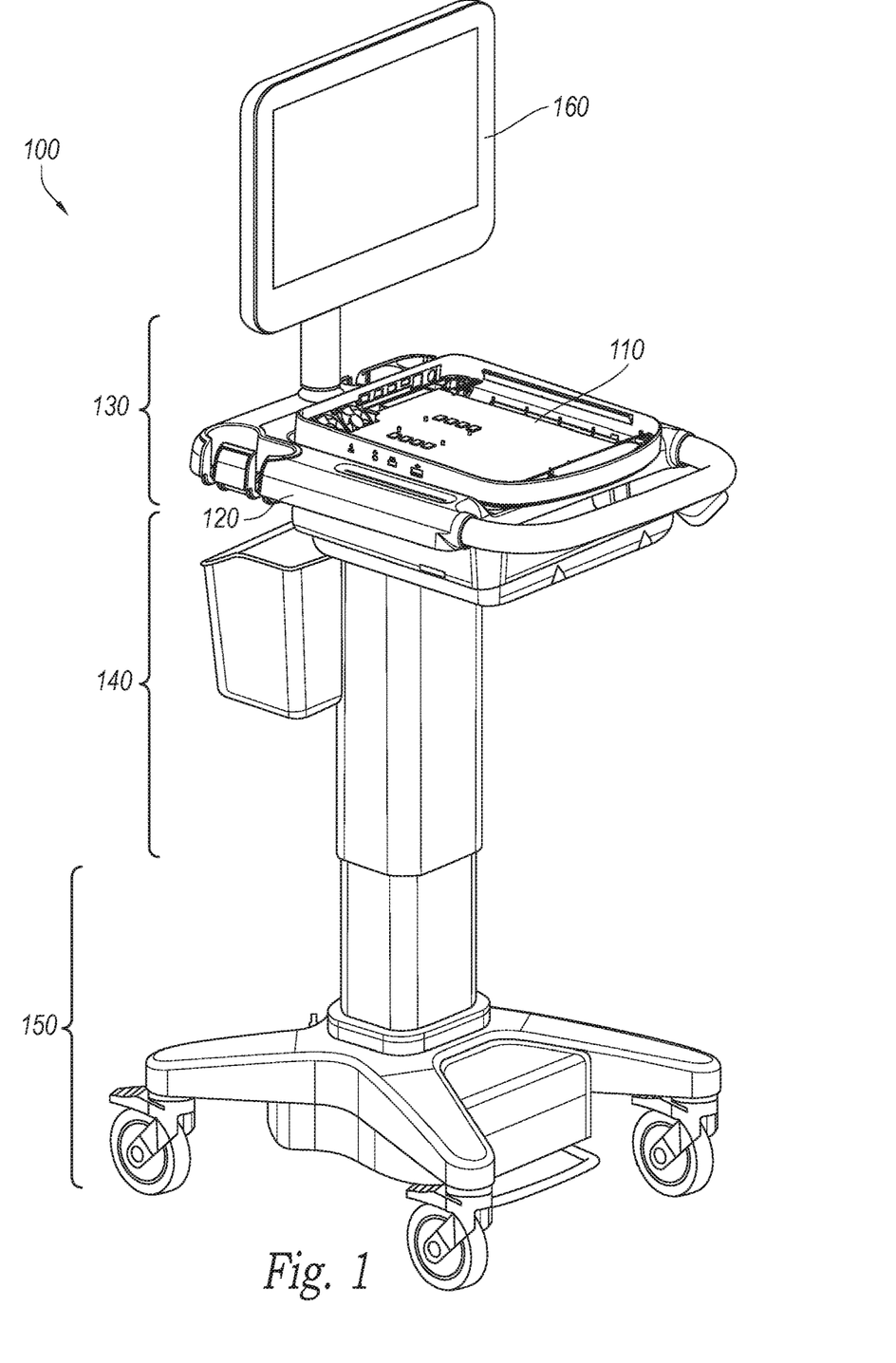
FIG. 1 is a side isometric view of a lower half of a housing of an ultrasonic imaging system docked to a stand, configured in accordance with an embodiment of the present technology.

FIG. 1 is front isometric view of a portion of a housing for a portable ultrasound device 110 ("the device 110") mounted to a stand 120. The stand 120 includes a stand head 130 and a base 150 that are connected by a support structure 140. The stand head 130 is formed to receive the device 110 such that an upper surface of the stand head 130 is generally complimentary to a lower surface of the device 110. For example, recesses in the stand head 130 can correspond to reciprocally shaped and positioned protrusions of the device 110 to be mounted thereon. As explained in further detail below, the device 110 is mountable on the stand head 130 in at least one of a first, undocked position and a second, docked position. In some embodiments, the device 110 can be moved from the undocked position to the docked position by applying a downward force to secure (e.g., snap) the device 110 onto the stand 120. The device 110 and/or stand 120 can include sensors or proximity switches (not shown) that recognize when the device 110 is in an undocked position or a docked position. As such, the device 110 and/or the stand 120 can perform automated functions (e.g., turn on fans) based on the position of the device 110. The device 110 is fully functional in either the docked or undocked positions. The stand 120 can also include a display unit 160 for displaying still or video images from the device 110 when mounted to the stand head 130 in either the docked or undocked positions.

Figure 2A:
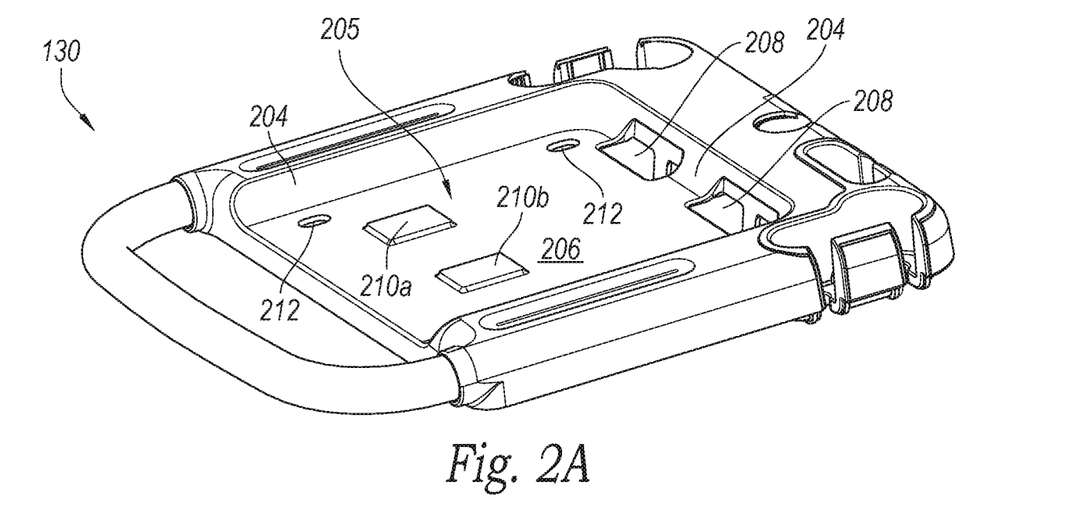
FIG. 2A is a top isometric view of a stand head configured in accordance with an embodiment of the present technology.

FIG. 2A is an top isometric view of the stand head 130. As shown in FIG. 2A, the stand head 130 includes an upper surface 206 and sidewalls 204 that together define a cavity 205. The cavity 205 is shaped to receive the device 110. In the illustrated embodiment, the cavity 205 includes one or more passageways 208 configured to allow air to move therethrough. As such, the passageways 208 can serve to cool the stand head 130, and/or any device mounted to the stand head 130, via convection. The stand head 130 includes one or more cold plates 210a-b (referred to together as "cold plate 210") (e.g., heat spreaders) positioned in the cavity 205. The cold plate 210 is embedded in the stand head 130 at the upper surface 206. As explained in further detail below with reference to FIG. 3C, at least a portion of the cold plate 210 protrudes upwards from the upper surface 206 of the stand head 130 and extends into the cavity 205. The cold plate 210 can be formed from a thermally conductive material such as metal, carbon, ceramic or a composite. In some embodiments, the cold plate 210 can be formed at least in part from, aluminum, copper, sheet metal, steel or any combination thereof. The stand head 130 can further include one or more shaped voids 212 extending at least partially through the upper surface 206 of the stand head 130 and corresponding to rubber feet (see FIG. 2D) on the device 110.

Figure 2B:
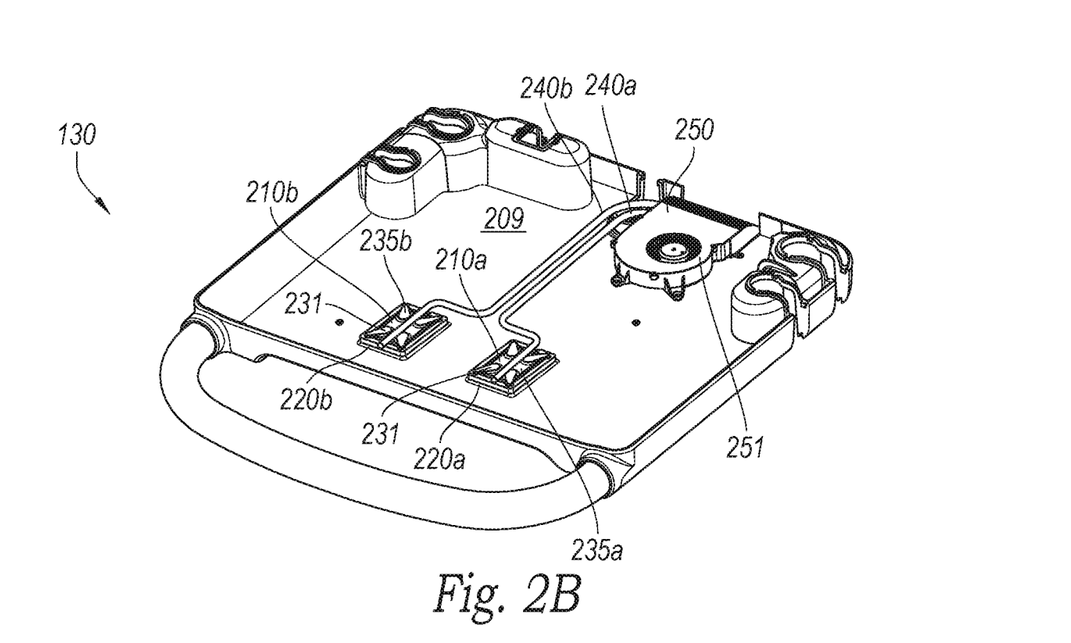
FIG. 2B is a bottom isometric view of the stand head shown in FIG. 2A, configured in accordance with an embodiment of the present technology.

FIG. 2B is a bottom isometric view of the stand head 130. As shown in FIG. 2B, the stand head 130 includes a lower surface 209, a first heat exchanger 250, and one or more first openings 220a-b (referred to together as "first opening 220") that extend through the stand head 130. The cold plate 210 is positioned in the first opening 220, and seals 235a-b (referred to together as "seal 235") (e.g., gaskets, etc.) are positioned around the cold plate 210 to prevent ingress of fluids between the upper surface 206 and the lower surface 209 of the stand head 130. Individual fasteners 231 can be used to secure the cold plate 210 to the lower surface 209 and/or other structures of the stand head 130.

The first heat exchanger 250 can include a structure or material that can store and/or transfer heat energy. As shown in FIG. 2B, the first heat exchanger 250 is thermally coupled to sealed cold pipes 240a-b (e.g., heat pipes) (referred to together as "cold pipes 240") and a fan 251. A working fluid is contained within the cold pipes 240 to aid in transferring heat from the cold plate 210 to a hot end of the pipes 240 proximate the cold plate 210, to a cold end of the pipes 240 opposite the hot end and adjacent the fan 251. Heat is transferred from the cold plate 210 to the first heat exchanger 250 at least via (a) convection from the working fluid within the cold pipes 240 and (b) conduction from outer walls of the cold pipes 240. Within the pipes 240, heat energy is transferred by means of phase transition of the working fluid and the release of latent heat at the cold end of the cold pipes 240. For example, the working fluid may exist in a partial vapor phase at the hot end of the cold pipes 240 proximate the cold plate 210, and may condense into a liquid phase at the cold end of the cold pipes 240 proximate the first heat exchanger 250. The phase transition occurring between the hot end and the cold end of the cold pipes 240 is based at least in part upon factors including the inner diameter of the cold pipes 240, the applied heat flux on the cold pipes 240, and the amount of working fluid within the cold pipes 240. These factors can be varied according to the desired application. In some embodiments, the cold pipes 240 may be maintained under at least a partial vacuum. The first heat exchanger 250 can further include a finned structure formed from a material with a high thermal conductivity (e.g., copper), and configured to absorb heat from the cold pipes 240. The finned structure can be positioned adjacent the fan 251, and be used to transfer heat energy to the surrounding environment. In operation, heat is transferred in a single-direction open loop manner away from the cold plate 210 and toward the finned structure and fan 251. The working fluid can include water, hydrocarbons, and/or other fluids and substances having an appropriate saturation point for the range of temperatures being considered for the desired application. In some embodiments, the first heat exchanger 250 can include other means to transfer heat away from the cold plate 210, including a closed loop liquid-cooled system, or a thermal reservoir (e.g., a high thermal conductivity block) configured to temporarily store a given amount of heat energy.

The cold pipes 240 shown in FIG. 2B have a cylindrical shape. However, a person of ordinary skill in the art will understand that the cold pipes 240 can exhibit other shapes. For example, the cold pipes 240 can include another shape that increases the amount of surface area in contact with the cold plate 210. Because the outer walls of the cold pipes 240 are meant to withdraw and transfer heat from the cold plate 210 via conduction, increasing the surface area of the cold pipes 240 that contacts the cold plate 210 will also increase the amount of heat that can be withdrawn from the cold plate 210 and transferred to the cold pipes 240 and working fluid contained therein.

Figure 2C:
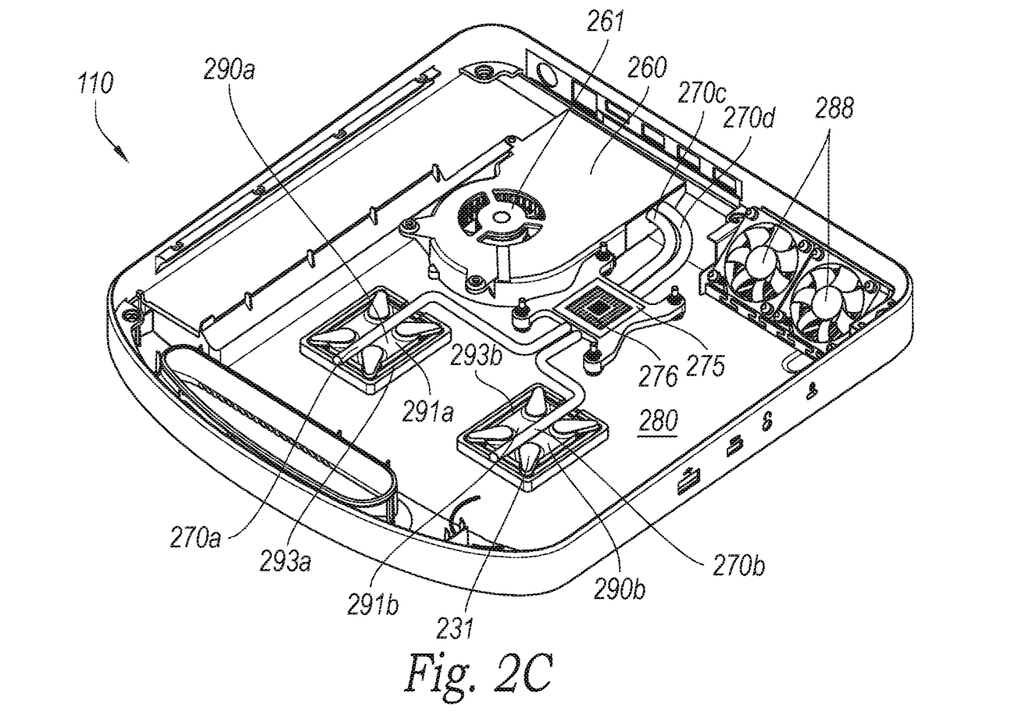
FIG. 2C is a top isometric view of a housing for a portable ultrasound system configured in accordance with an embodiment of the present technology.

FIG. 2C is a partial cut away view of the housing for device 110. The housing includes an upper surface 280, a second heat exchanger 260, one or more hot plates 290a-b (referred to together as "hot plate 290") (e.g., heat spreaders), and one or more second openings 291a-b (referred to together as "second opening") that extend through the bottom surface of the housing. The hot plate 290 is positioned within the second opening 291, and seals 293a-b (referred to together as "seal 293") are positioned around the hot plate 290 to prevent ingress of fluids into the housing of the device 110.

The second heat exchanger 260 can include similar structure and functionality to that of the first heat exchanger 250 described previously with respect to FIG. 2B. In some embodiments, the second heat exchanger 260 can include a fan 261 and a finned structure adjacent the fan 261. The second heat exchanger can be thermally coupled to a first plurality of sealed hot pipes 270a-b (e.g., heat pipes) (referred to together as "hot pipes 270") and a second plurality of sealed hot pipes 270c-d. The first plurality of hot pipes 270a-b thermally couples the hot plate 290 to the electronics of the device 110, and the second plurality of hot pipes 270c-d thermally couples the electronics of the device 110 to the second heat exchanger 260. As such, (a) the first plurality of hot pipes 270a-b includes a hot end proximate the electronics of the device 110, and a cold end opposite the hot end and proximate the hot plate 290, and (b) the second plurality of hot pipes 270c-d includes a hot end proximate the electronics of the device 110, and a cold end opposite the hot end and proximate the second heat exchanger 260. In operation, heat is transferred in a single-direction open loop manner away from the electronics of the device 110. For example, heat is transferred away from the electronics of the device 110 and toward the hot plate 290 via the first plurality of hot pipes 270a-b, and heat is transferred away from the electronics of the device 110 and toward the second heat exchanger 260 via the second plurality of hot pipes 270c-d. Heat is transferred from the hot ends of the hot pipes 270a-d to the cold ends using (a) convection from the working fluid within each of the hot pipes 270a-d, and (b) conduction from outer walls of each of the hot pipes 270a-d. As previously described with reference to FIG. 2B, one or more working fluids are contained within the hot pipes 270, and are configured to transfer heat from away from electronics of the device 110 via, for example, a phase transition. As explained in more detail below, when the device 110 is in a docked position, heat energy is transferred from the electronics of the device 110 to the hot plate 290 via hot pipes 270a-b, and further to the stand head 130. In some embodiments, the second heat exchanger 260 can include other means to transfer heat away from the electronics of the device 110, including a closed loop liquid-cooled system, or a thermal reservoir (e.g., a high thermal conductivity block) configured to temporarily store a given amount of heat energy.

The device 110 further includes a heat-generating source 276 (e.g., a processor, ASIC, DSP, graphics processor, FPGA or similar electronics) and a heat source contact plate 275 in contact with at least a portion of the heat-generating source 276. As previously described, the electronics or heat-generating source 276 is thermally coupled to (a) the second heat exchanger 260 at least via hot pipes 270c-d, and (b) the hot plate 290 at least via hot pipes 270a-b. As used herein, the term "thermally coupled" should be interpreted to mean capable of transferring heat energy.

The device 110 further includes one or more fan units 288 configured to move air through the device 110 and thereby provide a cooling driving force. The fan units 288 are generally aligned with the passageways 208 previously described with respect to FIG. 2A. The fan units 288 can be configured to automatically turn on and/or off based upon predetermined temperatures of the device 110.

Figure 2D:
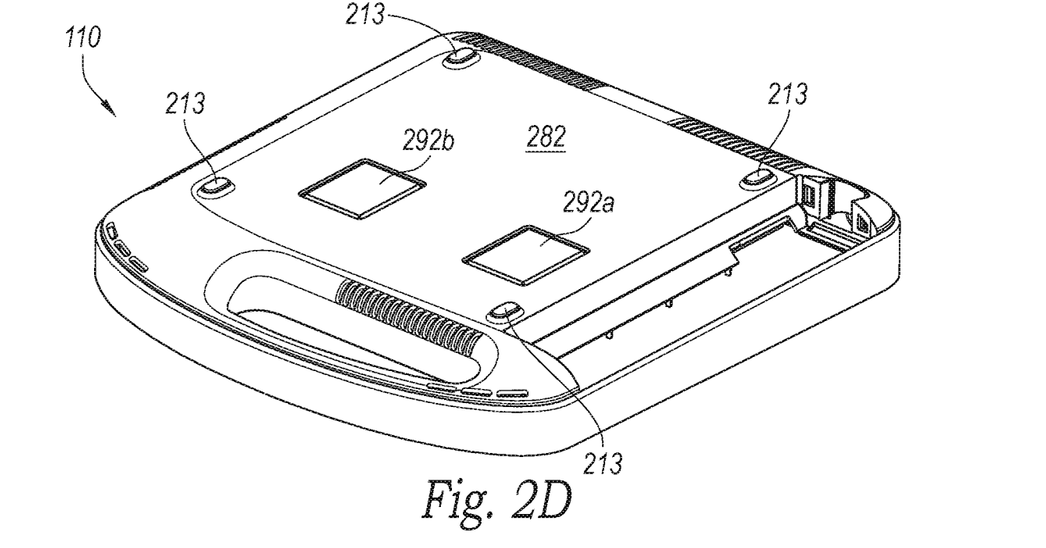
FIG. 2D is a bottom isometric view of the housing for a portable ultrasound system shown in FIG. 2C, configured in accordance with an embodiment of the present technology.

FIG. 2D is an isometric view of the bottom of the housing for the device 110. As shown in FIG. 2D, the housing includes a bottom surface 282, and barrier plates 292a-b (referred to together as "barrier plate 292") (e.g., a heat spreader, or inter-plate). The barrier plate 292 is positioned within the second opening 291 (FIG. 2C) and spaced from the hot plate 290 when the device 110 is in the undocked or docked position. As such, the barrier plate 292 is generally aligned with the hot plate 290. The term "generally aligned" as used herein should be interpreted to mean at least partially overlapping. As described in further detail below, the barrier plate 292 is movable to be in direct thermal contact with the hot plate 290 when the device 110 is docked. The barrier plate 292 can be formed from materials similar to those materials used to form the cold plate 210. In some embodiments, the barrier plate 292 is formed from copper, or similar materials with a high thermal mass and/or thermal conductivity. The housing of the device 110 also includes one or more outwardly extending protrusions 213 (e.g. feet) that are positioned complimentary to the voids 212 in the stand (FIG. 2A). Referring to FIGS. 2A and 2B together, the hot plate 290 on the device 110 is generally aligned with the cold plate 210 on the stand head 130 when the device 110 is mounted to the stand head in either the undocked position or the docked position.

Figure 3A:
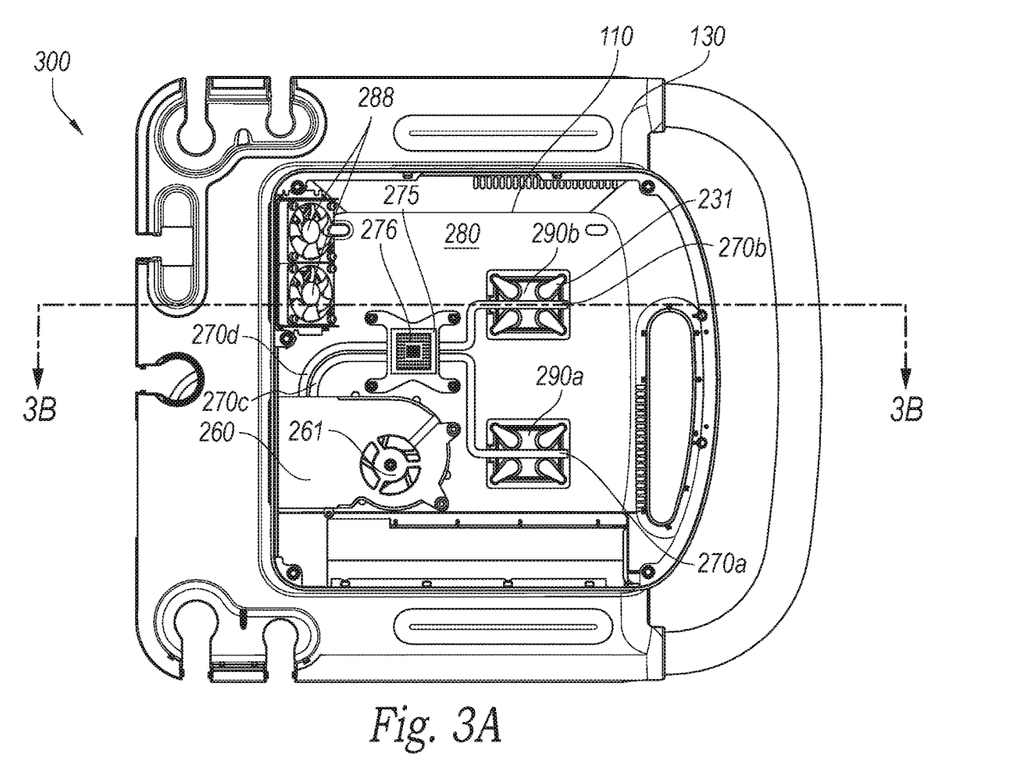
FIG. 3A is a top view of a cooling system in a portable ultrasound system mounted to a stand in an undocked position, configured in accordance with an embodiment of the present technology.
Figure 3B:
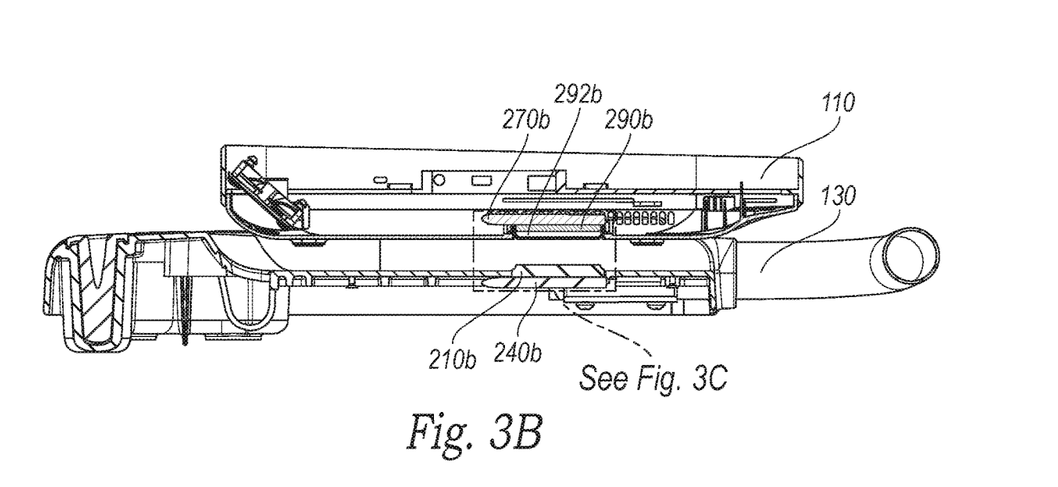
FIG. 3B is a cross-sectional view of the portable ultrasound system shown in FIG. 3A taken along line 3B-3B.
Figure 3C:
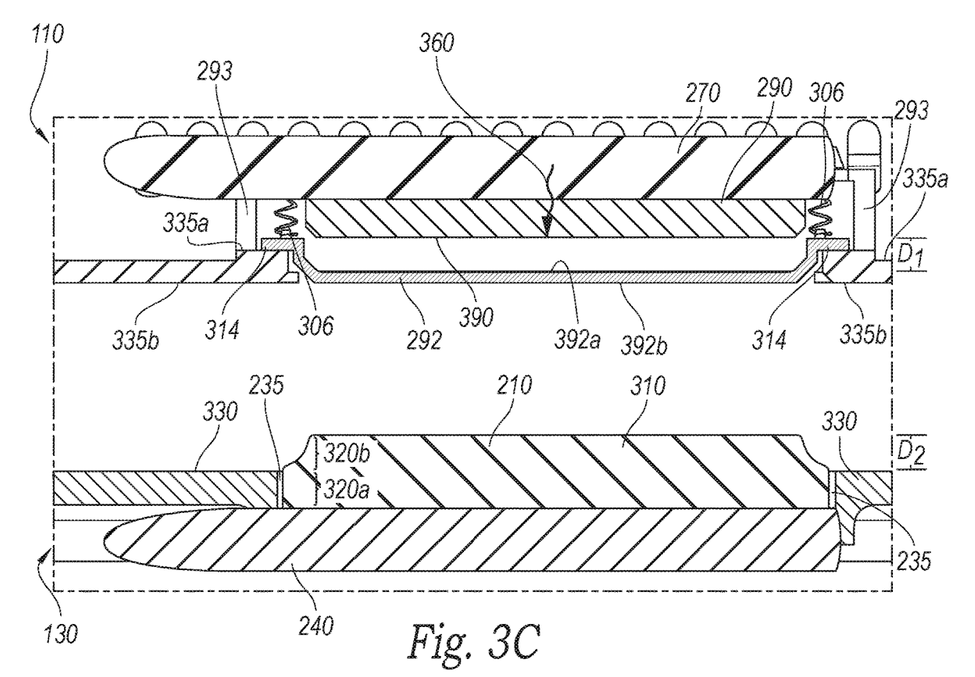
FIG. 3C is a magnified view of a portion of FIG. 3B.

FIG. 3A is a top view of the housing of the device 110 mounted to the stand head 130 in the first, undocked position. FIG. 3B is a cross sectional view of FIG. 3A taken along line 3B-3B. FIG. 3C is a magnified view of a portion of FIG. 3B. As shown in FIG. 3C, the hot plate 290 is fixedly-secured to a lower surface of the hot pipes 270. In the undocked position, the barrier plate 292 is positioned beneath and spaced apart from the hot plate 290 by a distance ($D_1$) that results in an air gap. The distance ($D_1$) should be small enough to prevent an operator from inserting his finger between the barrier plate 292 and the hot plate 290, and large enough to allow some surrounding air to pass between the barrier plate 292 and the hot plate 290 to cool the hot plate 290 via convection. In some embodiments, the distance ($D_1$) can be less than approximately one tenth inch or less. The limitation of how big the distance ($D_1$) is meant to comply with safety standards for medical electrical equipment, such as those set forth in IEC-60601.

The barrier plate 292 includes an inner surface 392a facing at least partially toward the hot plate 290, and an outer surface 392b facing at least partially toward the cold plate 210. The inner surface 392a has a shape generally similar to that of an opposed outer surface 390 of the hot plate 290. Each end of the barrier plate 292 includes a lip portion 314 that overlays and interfaces with at least a portion of a perimeter of the hole surrounding the hot plate 290 of the device 110.

In some embodiments, the barrier plate 292 is biased away from the hot plate 290 by one or more springs 306 (referred to together as "spring 306") attached to the barrier plate 292. More specifically, a first end of the spring 306 is attached to the lip portion 314 of the barrier plate 292, and a second end of the spring 306 is attached to a fixed structure of the housing of the device 110, such as a lower surface of the hot plate 290. The spring 306 provides a downward force on the lip portion 314 of the barrier plate 292 and biases the barrier plate 292 in a direction away from each of the hot pipes 270 and the hot plate 290. The downward force from the spring 306 secures the lip portion 314 of the barrier plate 292 against the hole surrounding the hot plate 290 of the device 110. In the undocked position, a portion of the outer surface 392b of the barrier plate 292 is generally flat, and co-planar with a portion of the bottom surface 335b of the housing of the device 110. The cold plate 210 in the stand is fixedly-secured to the cold pipes 240. The cold plate 210 includes a first portion 320a that lies beneath the top surface of the stand head 130, and a second portion 320b that protrudes from the upper surface 330 of the stand head 130 by a distance ($D_2$). The distances $D_1$ and $D_2$ are approximately equal. An outer surface 310 of the cold plate 210 is generally flat.

When the device 110 is not mounted to the stand head 130 and is therefore in the undocked position, the bottom surface 335b of the device 110 is proximate to and physically separated from the upper surface 330 of the stand head 130. Similarly, in the undocked position, the barrier plate 292 is physically separated from the hot plate 290. As such, in the undocked position, a conductive path 360 exists between the hot pipes 270 and the hot plate 290, but not the barrier plate 292. Therefore, in the undocked position, a majority of heat transferred to the hot plate 290 is then transferred to the surrounding air via only convection.

Figure 4A:
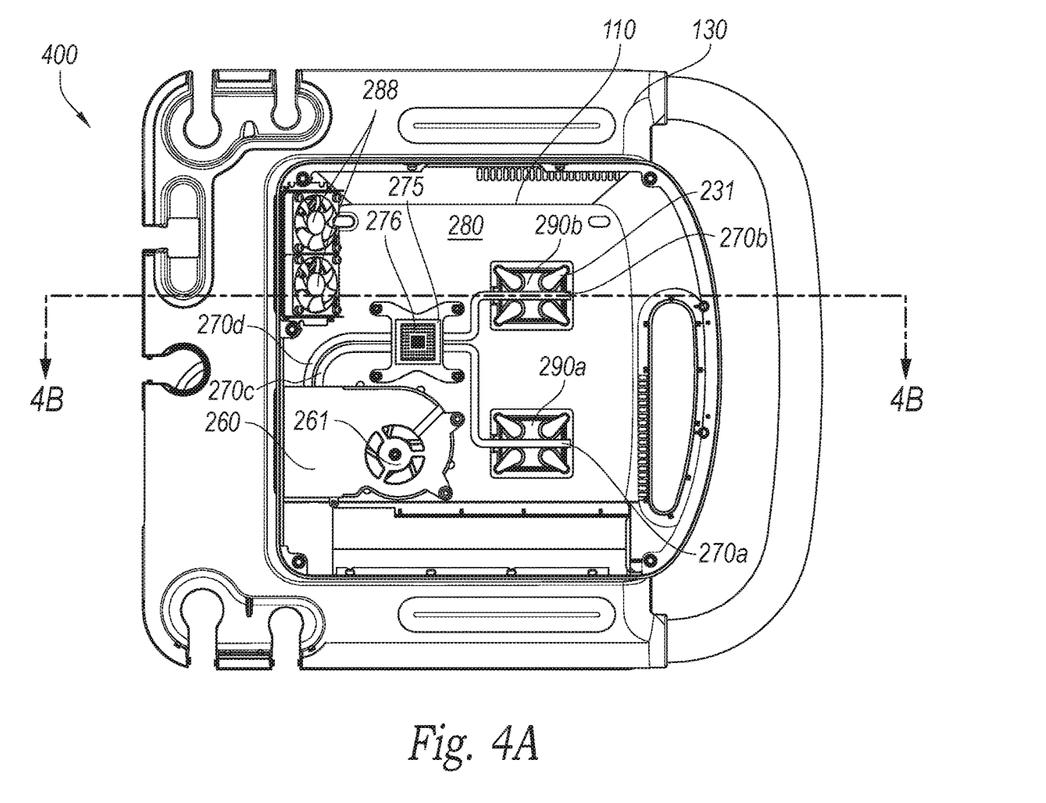
FIG. 4A is a top view of a housing for a portable ultrasound system mounted to a stand in a docked position in accordance with an embodiment of the present technology.
Figure 4B:
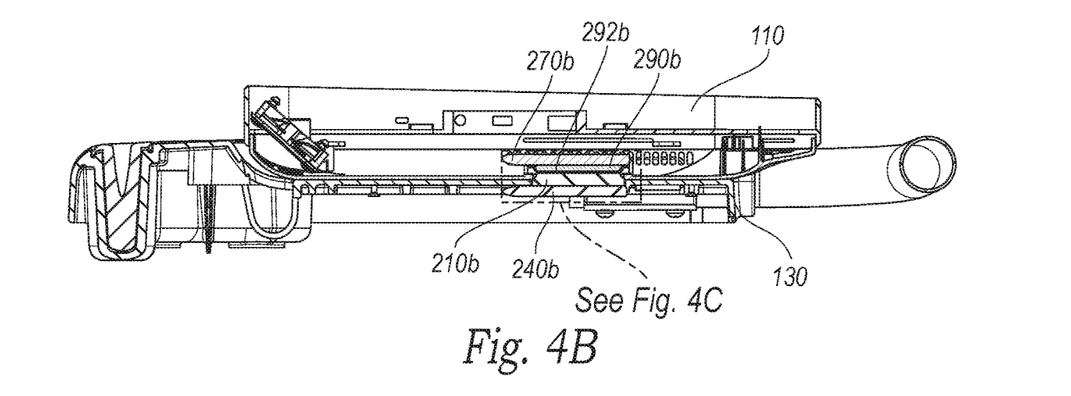
FIG. 4B is a cross-sectional view of the portable ultrasound system shown in FIG. 4A taken along line 4B-4B, in accordance with an embodiment of the present technology.
Figure 4C:
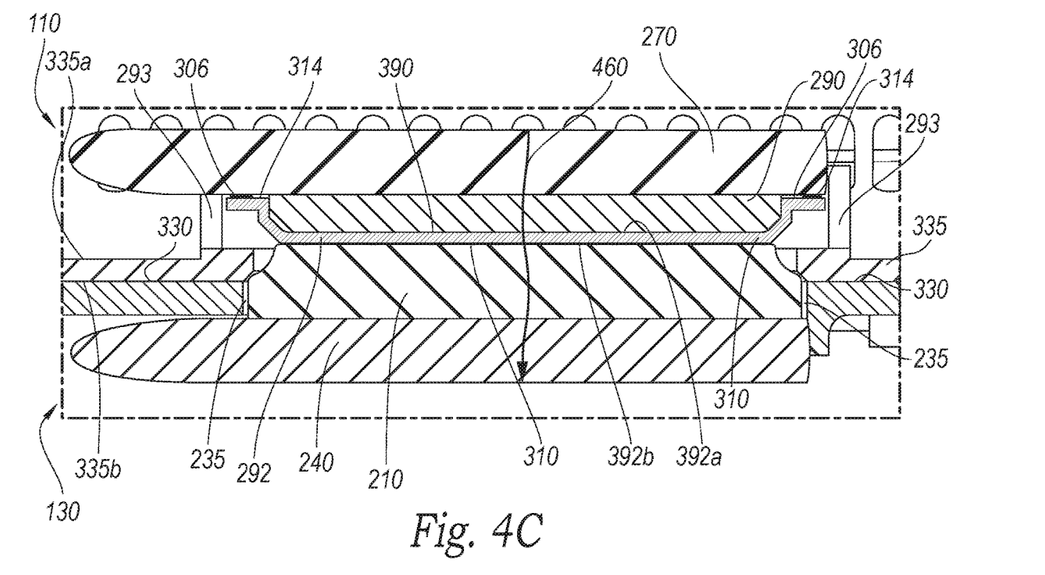
FIG. 4C is a magnified view of a portion of FIG. 4B.

FIG. 4A is a top view of a portion of the housing of device 110 mounted to the stand 120 in the second, docked position. FIG. 4B is a cross sectional view of FIG. 4A taken along line 4B-4B. FIG. 4C is a magnified view of a portion of FIG. 4B. After the housing for the device 110 is mounted to the stand head 130, and as the device 110 is moved from the undocked position to the docked position, the top surface of the cold plate 210 contacts and pushes the barrier plate 292 toward the hot plate 290. As the cold plate 210 pushes the barrier plate 292 upward toward the hot plate 290, the downward force of the spring 306 is overcome and the spring 306 is compressed. Even in the docked position, the spring 306 provides a downward force that pushes the barrier plate 292 against the cold plate 210 to ensure there is a good thermal contact between the barrier plate 292 and the cold plate 210. This downward force results in a clamping pressure that improves the conductive heat transfer between the barrier plate 292 and the cold plate 210 in the docked position.

Once in the docked position, the barrier plate 292 remains in thermal contact with each of the cold plate 210 and the hot plate 290. As such, the barrier plate 292 acts as a thermal conductive bridge between the cold plate 210 and the hot plate 290. The inner surface 392a of the barrier plate 292 and the outer surface 390 of the hot plate 290 meet at an interface that spans across at least a majority of each of the surfaces. The inner surface 392a of the barrier plate 292 includes a shape that is generally similar and complimentary to the shape of the outer surface 390 of the hot plate 290. For example, each of the inner surface 392a and the outer surface 390 include vertical, diagonal, and horizontal edges that complement and correspond to one another. As such, the interface between the barrier plate 292 and the hot plate 290 spans substantially across the entire inner surface 392b of the barrier plate 292 and the outer surface 390 of the hot plate 290. Maximizing the area of this interface increases the conductive heat transfer rate between the barrier plate 292 and the hot plate 290. Similarly, the outer surface 392b of the barrier plate 292 is in contact with an outer surface 310 of the cold plate 210 at an interface that spans substantially across the entire outer surface 392b of the barrier plate 292 and the entire outer surface 310 of the cold plate 210. In the docked position, the upper surface 330 of the stand head 130 is in contact with the bottom surface 335b of the housing of the device 110. It is possible for both (a) the upper surface 330 of the stand head 130 and the bottom surface 335b of the device 110, and (b) the hot plate 290, the barrier plate 292, and the cold plate 210 to be in contact with another in part because, in the undocked position, the distance ($D_1$) between the outer surface 390 of the hot plate 290 and the inner surface 392a of the barrier plate 292 is equal to the distance ($D_2$) between the outer surface 392b of the cold plate 210 and the upper surface 330 of the stand head 130 (FIG. 3C).

When the device 110 is mounted to the stand head 130 in the docked position, the bottom surface 335b of the device 110 is immediately adjacent the upper surface 330 of the stand head 130, and the barrier plate 292 is in direct contact with the hot plate 290 and the cold plate 210. As such, in the docked position, a conductive path 460 exists between the hot pipes 270, the hot plate 290, the barrier plate 292, the cold plate 210, and the cold pipes 240. Therefore, in the docked position, at least some heat from the heat-generating source 276 is transferred to the cold plate 210, and the cold pipes 240 in the stand by conduction.

From the foregoing, it will be appreciated that specific embodiments of the invention have been described herein for purposes of illustration, but that various modifications may be made without deviating from the scope of the invention. Accordingly, the invention is not limited except as by the appended claims. A person of ordinary skill will recognize that in other embodiments, the device 110 and/or the stand head 130 can be configured differently. For example, though many of the embodiments show multiple structures that perform the same function (e.g., hot plates 290a-b, barrier plates 292a-b, cold plates 210a-b, etc.), other embodiments may include more structures (e.g., three or four) or less structures (e.g., one) to perform the same function. Similarly, a person of ordinary skill in the art will appreciate that any combination of these different configurations can be incorporated into the present technology.

This disclosure is not intended to be exhaustive or to limit the present technology to the precise forms disclosed herein. Although specific embodiments are disclosed herein for illustrative purposes, various equivalent modifications are possible without deviating from the present technology, as those of ordinary skill in the relevant art will recognize. In some cases, well known structures and functions have not been shown or described in detail to avoid unnecessarily obscuring the description of the embodiments of the present technology. Although steps of methods may be presented herein in a particular order, alternative embodiments may perform the steps in a different order. Similarly, certain aspects of the present technology disclosed in the context of particular embodiments can be combined or eliminated in other embodiments. Furthermore, while advantages associated with certain embodiments of the present technology may have been disclosed in the context of those embodiments, other embodiments can also exhibit such advantages, and not all embodiments need necessarily exhibit such advantages or other advantages disclosed herein to fall within the scope of the technology. Accordingly, the disclosure and associated technology can encompass other embodiments not expressly shown or described herein.

Throughout this disclosure, the singular terms "a," "an," and "the" include plural referents unless the context clearly indicates otherwise. Similarly, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. Reference herein to "one embodiment," "an embodiment," or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics may be combined in any suitable manner in one or more embodiments.

I claim:

1. A portable imaging ultrasound system configured to be mounted to a stand, the system comprising:
   heat-generating electronics that process ultrasound signals;
   a hot plate for spreading heat collected by the heat-generating electronics; and
   a barrier plate adjacent to the hot plate and moveable between a first position and a second position, wherein
   in the first position, the barrier plate is spaced apart from the hot plate, and
   in the second position, the barrier plate is in thermal conductive contact with the hot plate, wherein a planar outer surface forming one side of the hot plate and a planar outer surface forming one side of the barrier plate interfaces with each other for the thermal conductive contact when in the second position and wherein the barrier plate interfaces a cold plate of the stand when in the second position.

2. The system of claim 1, further comprising a heat pipe thermally coupled to the heat-generating electronics and the hot plate.

3. The system of claim 1, further comprising a heat pipe having a hot end thermally coupled to the heat-generating electronics, and a cold end thermally coupled to a heat exchanger on the ultrasound system, wherein the heat pipe is configured to transfer heat away from the heat-generating electronics using a working fluid contained within the heat pipe.

4. The system of claim 3 wherein the working fluid undergoes at least a partial phase transition between (a) a vapor phase at the hot end of the heat pipe and (b) a liquid phase the cold end of the heat pipe.

5. The system of claim 1 wherein, in the second position, the system is in a docked position.

6. The system of claim 1 wherein, in the first position, the system is in an undocked position and the barrier plate is separated from the hot plate by an air gap approximately less than one tenth inch.

7. The system of claim 1 wherein, in the second position, a conductive path exists between the heat-generating electronics and the stand via at least the hot plate, and the barrier plate.

8. The system of claim 1 wherein the barrier plate is biased away from the hot plate by a spring.

9. The system of claim 1 wherein the heat-generating electronics includes a processor.

10. A portable ultrasound device configured to be mounted to a stand, the device comprising:
    a heat-generating source;
    a hot plate proximate and thermally coupled to the heat-generating source; and
    a barrier plate biased away from the hot plate and moveable from a first undocked position to a second docked position, wherein
    in the first position, the barrier plate is spaced apart from the hot plate, and
    in the second position, a first planar outer surface forming one side of the barrier plate is in contact with a first planar outer surface forming one side of the hot plate and the barrier plate is in contact with a cold plate of the stand.

11. The device of claim 10 wherein, in the second position, the barrier plate is in contact with the stand and between the hot plate and the stand.

12. The device of claim 10 wherein, in the second position, a conductive path exists between the heat-generating source and the stand via at least the hot plate and the barrier plate.

13. The device of claim 10, further comprising a hot pipe thermally coupled to the heat-generating source and the hot plate.

14. The system of claim 13 wherein the hot pipe includes a working fluid configured to transfer heat energy from the heat-generating source to the hot plate at least in part by transitioning between a first phase and a second phase within the hot pipe.

15. The system of claim 10 wherein the device includes a bottom surface and the barrier plate includes a second planar outer surface, and wherein, in the first position, the bottom surface of the device is generally co-planar with at least a portion of the second planar outer surface of the barrier plate.

16. A method for docking a medical device to a stand head configured to receive the device, the method comprising:
    moving the device to a docked position on the stand head, thereby causing a first planar surface that forms one side of a barrier plate of the medical device to contact a first planar surface that forms one side of a hot plate of the medical device; and
    transferring heat from a heat-generating source of the device to the stand head via a conductive pathway including the hot plate, the barrier plate, and a cold plate of the stand.

17. The method of claim 16 wherein causing a barrier plate to contact a hot plate includes pushing the barrier plate with a portion of the stand to move the barrier plate toward the hot plate.

18. The method of claim 17 wherein the portion of the stand moving the barrier plate is the cold plate of the stand.

19. The method of claim 16 wherein moving the medical device on the stand head to a docked position causes a portion of the stand to contact the barrier plate.

20. The method of claim 16 wherein transferring heat includes transferring heat to the hot plate via a working fluid contained within a heat pipe thermally coupled to the heat-generating source.

21. The method of claim 16 wherein the conductive pathway further includes a cold plate of the stand.

22. The method of claim 16 wherein causing a first planar surface of a barrier plate to a first planar surface of a contact a hot plate includes compressing one or more springs that bias the barrier plate away from the hot plate prior to when the barrier plate contacts the hot plate.

23. A system configured to receive an ultrasound portable device having heat-generating electronics, a hot plate thermally coupled to the heat-generating source, and a barrier plate, the stand comprising:
    a base portion;
    a support structure attached to the base portion; and
    a stand head attached to the support structure, wherein the stand head includes a cold plate and a cold pipe thermally coupled to the cold plate, wherein the cold pipe is configured to transfer heat away from the cold plate, and wherein the stand head is configured to receive the portable device in at least one of an undocked position or a docked position such that
    in the undocked position, the cold plate is separated from a barrier plate of the device, and
    in the docked position, a planar outer surface of the cold plate is in contact with a planar outer surface of the barrier plate of the device and the barrier plate is in contact with the hot plate of the device.

24. The system of claim 23 wherein the cold plate includes a first portion that extends at least partially below a surface of the stand head and a second portion that extends above an upper surface of the stand head.

25. The system of claim 24 wherein the second portion of the cold plate extends above an upper surface of the stand head by a first distance, and wherein, in the undocked position, the barrier plate is spaced apart from the hot plate by the first distance.

26. A portable ultrasound imaging system, comprising:
    one or more heat-generating electronics for receiving one or more signals related to ultrasound;
    a hot plate for spreading heat collected from the one or more heat-generating electronics; and
    a barrier plate for spreading heat collected by the hot plate, wherein
    in a first position, the barrier plate is spaced apart from the hot plate, and in a second position, a planar outer surface forming one side of the barrier plate is in thermal contact with a planar outer surface forming one side of the hot plate and the barrier plate is in contact with a cold plate of a stand.

27. An ultrasound imaging system, comprising:
a housing;
electronics in the housing that process ultrasound signals to produce ultrasound images;
a heat dissipating surface in the housing that dissipates heat from the electronics; and
a thermally conductive barrier plate adjacent the heat dissipating surface that is movable from (a) a first position where there is an airgap between the barrier plate and the heat dissipating surface and (b) a second position where a planar outer surface of the barrier plate is in thermal contact with a planar outer surface of the heat dissipating surface such that when in the second position, heat is transferred to the barrier plate by conduction and the barrier plate is in contact with a cold plate of a stand.

28. The ultrasound imaging system of claim 27 wherein the barrier plate is positioned between the heat dissipating surface and an exterior of the housing to prevent user contact with the heat dissipating surface.

29. A stand for a medical device of the type having a thermal spreader and a barrier plate positioned on a housing of the medical device between the thermal spreader and an exterior of the housing, the stand comprising:
a base;
a stand head supported by the base and including a surface onto which a medical device can be docked; and
a cold plate in the stand head for at least partially absorbing heat generated in the medical device,
wherein a planar outer portion of the cold plate extends above the surface of the stand head and engages with a planar outer surface of the barrier plate on the medical device configured to complete a conductive thermal path from the cold plate to the barrier plate, to the heat spreader in the medical device.

30. The portable imaging ultrasound system of claim 1 further comprising a housing, wherein the heat-generating electronics are contained in the housing and the barrier plate has a second planar outer surface, the second planar outer surface being co-planar with a bottom surface of housing when the barrier plate is in the first position, the planar outer surface of the barrier plate and the second planar outer surface being on opposite sides of the barrier plate.

31. The portable imaging ultrasound system of claim 30 wherein the barrier plate is movable to the second position in response to a planar outer surface of a cold plate having pushed the second planar outer surface of the barrier plate towards the hot plate to a point where the cold plate protrudes into the housing and the hot plate, the barrier plate and the cold plate are in thermal conductive contact with each other.

* * * * *